United States Patent
Cordi et al.

(10) Patent No.: US 6,518,258 B1
(45) Date of Patent: Feb. 11, 2003

(54) 6-SULPHAMOYL-3-QUINOLYPHOSPHONIC ACID COMPOUNDS

(75) Inventors: Alex Cordi, Suresnes (FR); Patrice Desos, Courbevoie (FR); Pierre Lestage, La Celle Saint Cloud (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/783,650

(22) Filed: Feb. 14, 2001

(30) Foreign Application Priority Data

Feb. 18, 2000 (FR) .............................. 00 02011

(51) Int. Cl.⁷ .......................... A61K 31/675; C07F 9/60
(52) U.S. Cl. .......................... 514/89; 546/21
(58) Field of Search ............... 546/21; 514/89

(56) References Cited

U.S. PATENT DOCUMENTS

2001/0031746 A1 * 10/2001 Cordi et al. .......... 514/82

* cited by examiner

Primary Examiner—Patricia L. Morris
(74) Attorney, Agent, or Firm—The Firm of Hueschen and Sage

(57) ABSTRACT

The invention relates to a compound of formula (I):

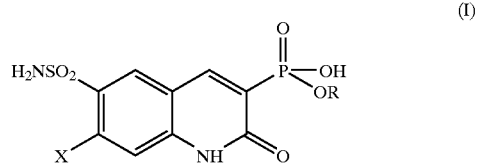

wherein:
- X represents chlorine or fluorine or $CF_3$,
- R represents hydrogen or a group

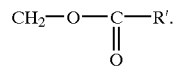

and methods for using the same.

7 Claims, No Drawings

6-SULPHAMOYL-3-QUINOLYPHOSPHONIC ACID COMPOUNDS

FIELD OF THE INVENTION

The present invention relates to new 6-sulphamoyl-3-quinolylphosphonic acid compounds and to compositions containing them.

DESCRIPTION OF THE PRIOR ART AND BACKGROUND OF THE INVENTION

The present invention constitutes a selection with respect to the patent EP 0 640 612. Patent specification EP 0 640 612 describes compounds that are capable of countering the excitatory and toxic effects of the excitatory amino acids (EAA) by blocking the initial activation of the AMPA ((α-amino-3-hydroxy-5-methyl-4-isoxazole-propionic acid)/kainate receptor. Their usefulness is accordingly recognized for inhibiting pathological phenomena, especially neurotoxic phenomena associated with hyperactivation of the neurotransmission paths to the excitatory amino acids. The Applicant has, however, found serious problems of nephrotoxicity associated with the use of those compounds, for example in the case of (6,7-dichloro-2-oxo-1,2-dihydro-3-quinolyl)phosphonic acid, as has also been shown to be the case, moreover, for other non-NMDA (N-methyl-D-aspartate) antagonists of reference, for example 6-nitro-7-sulphamoyl-benzo[f] quinoxaline-2,3-dione (NBQX) (Journal of Cerebral Blood Flow and Metabolism, 1994, 14, 251–261).

The Applicant has discovered, surprisingly, that a small group of compounds not described in patent specification EP 0 640 612 not only have powerful non-NMDA antagonist properties but are completely without associated nephrotoxicity. These compounds are therefore new and are potential powerful therapeutic agents for acute, and also chronic, treatment of neurological and psychological disorders involving those amino acids, for example degenerative disorders such as cerebrovascular accident, cerebral or spinal traumatism, epilepsy, chronic neurodegenerative diseases such as Alzheimer's disease, schizophrenia, lateral amyotrophic sclerosis or Huntington's chorea.

DETAILED DESCRIPTION OF THE INVENTION

More specifically, the present invention relates to compounds of formula (I):

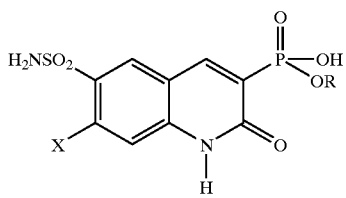

wherein:
- ♦ X represents a chlorine or fluorine atom or a trifluoromethyl group,
- ♦ R represents a hydrogen atom or a group

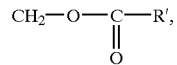

wherein R' represents a hydrogen atom or a linear or branched ($C_1$-$C_6$)alkyl or phenyl group, their isomers and addition salts thereof with a pharmaceutically acceptable base.

Among the pharmaceutically acceptable bases there may be mentioned, without implying any limitation, sodium hydroxide, potassium hydroxide, triethylamine, tert-butylamine etc.

Preferred compounds of the invention are compounds of formula (I) wherein R represents a hydrogen atom.

More particularly, the invention relates to the compounds of formula (I) which are:
- (7-chloro-2-oxo-6-sulphamoyl-1,2-dihydro-3-quinolyl) phosphonic acid,
- (7-trifluoromethyl-2-oxo-6-sulphamoyl-1,2-dihydro-3-quinolyl)phosphonic acid,
- (7-fluoro-2-oxo-6-sulphamoyl-1,2-dihydro-3-quinolyl) phosphonic acid.

The isomers, as well as the addition salts with a pharmaceutically acceptable base, of the preferred compounds form an integral part of the invention.

The invention relates also to a process for the preparation of compounds of formula (I), characterised in that there is used as starting material a compound of formula (II):

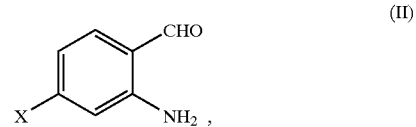

wherein X is as defined for formula (1), which is condensed, in the presence of a base, such as, for example, pyridine, with a compound of formula (III):

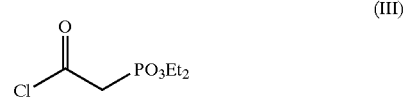

to yield a compound of formula (IV):

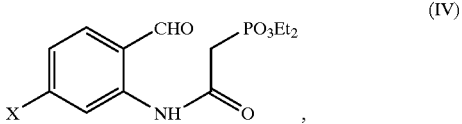

wherein X is as defined hereinbefore, which is cyclised in the presence of a catalytic amount of piperidine to obtain a compound of formula (V):

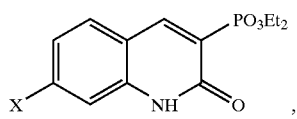
(V)

wherein X is as defined hereinbefore, which is subjected to a mixture of nitric acid and sulphuric acid to yield a compound of formula (VI):

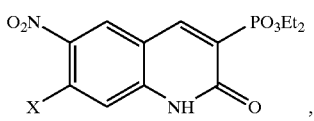
(VI)

wherein X is as defined hereinbefore, which is reduced using palladium-on-carbon in the presence of hydrogen or iron in a dilute alcoholic medium to obtain a compound of formula (VII):

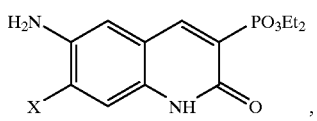
(VII)

wherein X is as defined hereinbefore, which is subjected, after conversion into the corresponding diazonium salt, to the action of sulphur dioxide in the presence of $CuCl_2$ to yield a compound of formula (VIII):

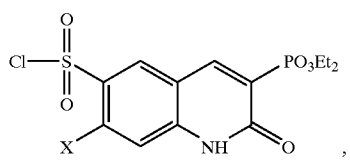
(VIII)

wherein X is as defined hereinbefore, which is placed in the presence of ammonium hydroxide solution to obtain a compound of formula (IX):

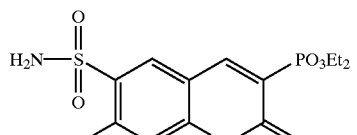
(IX)

wherein X is as defined hereinbefore, which is deprotected in the presence of trimethylsilane bromide in an acetonitrile medium to yield a compound of formula (I/a), a particular case of the compounds of formula (I):

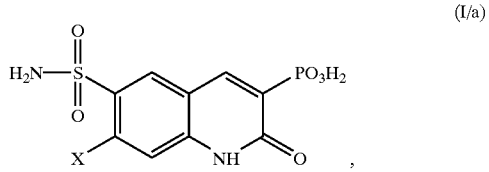
(I/a)

wherein X is as defined hereinbefore,
which may be reacted in a basic medium with a compound of formula (X):

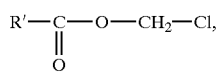
(X)

wherein R' is as defined for formula (I),
to yield a compound of formula (I/b), a particular case of the compounds of formula (I):

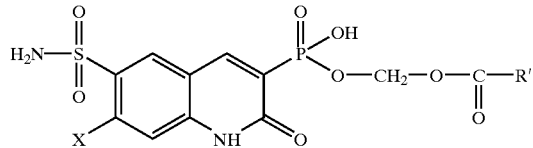
(I/b)

wherein X and R' are as defined hereinbefore,
which compounds of formulae (I/a) and (I/b) constitute the totality of the compounds of formula (I), and can be purified according to a conventional separation technique, are converted, if desired, into their addition salts with a pharmaceutically acceptable base, and separated, where appropriate, into their isomers according to a conventional separation technique.

The compounds of the invention have very valuable pharmacological properties since they are powerful inhibitors of the AMPA receptor, and they are moreover selective since they do not affect the NMDA receptor and therefore do not have any of the side-effects described for NMDA antagonists; above all, they do not have the nephrotoxicity associated with a number of AMPA/non-NMDA antagonists. The use of those compounds as inhibitors of pathological phenomena associated with hyperactivation of the neurotransmission paths to the excitatory amino acids will therefore be particularly appreciated in the acute, and especially chronic, treatment of neurological and psychological disorders involving those amino acids, for example degenerative disorders such as cerebrovascular accident, cerebral or spinal traumatism, epilepsy, chronic neurodegenerative diseases such as Alzheimer's disease, schizophrenia, lateral amyotrophic sclerosis or Huntington's chorea.

The present invention relates also to pharmaceutical compositions comprising as active ingredient at least one compound of formula (I) alone or in combination with one or more pharmaceutically acceptable excipients.

Among the pharmaceutical compositions according to the invention, there may be mentioned more especially those that are suitable for oral, parenteral, nasal, per- or trans-cutaneous, rectal, perlingual, ocular or respiratory administration, and especially tablets or degrees, sublingual tablets, sachets, paquets, gelatin capsules, glossettes, lozenges, suppositories, creams, ointments, dermal gels and drinkable or injectable ampoules.

The dosage varies according to the sex, age and weight of the patient, the route of administration, the nature of the therapeutic indication, or any associated treatments, and ranges from 50 mg to 1 g per 24 hours in 1 or more administrations.

The following Examples illustrate the invention and do not limit it in any way.

EXAMPLE 1

(7-Chloro-2-oxo-6-sulphamoyl-1,2-dihydro-3-quinolyl)phosphonic Acid

Step A: [(5-Chloro-2-formyl-phenylcarbamoyl)methyl] phosphonic Acid Diethyl Ester Pyridine (3.7 ml, 45.7 mmol) is added to a solution of 2-amino-4-chloro-benzaldehyde (6.18 g, 39.7 mmol) in 170 ml of anhydrous toluene, followed dropwise by a solution of chlorocarbonylmethylphosphonic acid diethyl ester (9.8 g, 45.7 mmol) in 15 ml of anhydrous toluene whilst maintaining the reaction mixture at a temperature of less than 30° C. When the addition is complete, the mixture is stirred for 1 hour at room temperature. The reaction mixture is washed several times with water and then with a 1N HCl solution, and then again with water. Finally the mixture is washed with an aqueous saturated NaCl solution. The organic phase is dried over $MgSO_4$, and filtration is carried out, followed by evaporation to obtain the expected crude product in the form of an orange oil. The crude product is used in the following step.

Step B: (7-Chloro-2-oxo-1,2-dihydro-3-quinolyl) phosphonic Acid Diethyl Ester

In a round-bottomed flask on which there is mounted a Dean-Stark apparatus there is refluxed for 4 hours, with vigorous stirring, all of the compound obtained in Step A dissolved in 300 ml of toluene and 0.3 ml of piperidine. The batch is left to crystallise at room temperature and the pale yellow solid obtained is filtered off.

Melting point: 210–213° C.; Elemental microanalysis:

|  | C % | H % | N % | Cl % |
|---|---|---|---|---|
| calculated | 49.46 | 4.79 | 4.44 | 11.23 |
| found | 49.77 | 4.78 | 4.46 | 11.63 |

Step C: (7-Chloro-6-nitro-2-oxo-1,2-dihydro-3-quinolyl) phosphonic Acid Diethyl Ester 55 ml of nitric acid are added dropwise to a solution of 55 ml of 96% sulphuric acid cooled in an ice bath, and then (7-chloro-2-oxo-1,2-dihydro-3-quinolyl)phosphonic acid diethyl ester (14.7 g, 46.6 mmol) is added in portions whilst maintaining the temperature at less than or equal to 5° C. When the addition is complete, stirring is continued for 15 minutes and then the ice bath is withdrawn and the reaction mixture is brought to ambient temperature over a period of about 1 hour 30 minutes. The solution is poured into ice and the precipitate is stirred to obtain a filterable solid. Filtration is carried out, followed by washing with water to neutrality and drying in vacuole. The solid is suspended in 210 ml of ethanol at reflux; the batch is left to cool and, after drying, filtered to obtain the title compound.

Melting point: 258–262° C.; Elemental microanalysis:

|  | C % | H % | N % | Cl % |
|---|---|---|---|---|
| calculated | 43.29 | 3.91 | 7.77 | 9.83 |
| found | 43.33 | 4.06 | 7.60 | 9.70 |

Step D: (6-Amino-7-chloro-2-oxo-1,2-dihydro-3-quinolyl) phosphonic Acid Diethyl Ester A suspension of the compound obtained in Step C (7.0 g, 19.4 mmol), powdered iron (10.8 g, 194 mmol) and ammonium chloride (10.4 g, 194 mmol) is stirred at reflux for 1 hour in a mixture of 270 ml of methanol and 90 ml of water. The suspension is filtered hot over Celite and the solid is rinsed several times with methanol. The filtrate is evaporated to dryness and the residue is suspended in water. The solid is filtered off, rinsing with water and drying to obtain the title product in the form of orange crystals.

Melting point: 255–260° C.; Elemental microanalysis:

|  | C % | H % | N % |
|---|---|---|---|
| calculated | 47.22 | 4.88 | 8.47 |
| found | 47.06 | 4.99 | 8.08 |

Step E: (7-Chloro-6-chlorosulphonyl-2-oxo-1,2-dihydro-3-quinolyl)phosphonic Acid Diethyl Ester A solution of 13.4 ml of acetic acid and 2.25 ml of water is saturated with $SO_2$ by bubbling in $SO_2$ gas for 15 minutes. In parallel, a solution of the compound obtained in Step D (3.34 g, 10.1 mmol) in a mixture of 10 ml of glacial acetic acid and 17 ml of concentrated HCl is prepared at 5° C. A solution of sodium nitrite (767 mg, 11.11 mmol) previously dissolved in 5 ml of water is added dropwise to the resulting solution and the reaction mixture is stirred at 5° C. for 30 minutes. $CuCl_2 \cdot 2H_2O$ (689 mg, 4.04 mmol) is added to the $SO_2$-saturated solution, and the suspension obtained is cooled to 5° C. To the resulting suspension there is added, dropwise, the diazonium chloride solution prepared above. The mixture is stirred for 1 hour at 5° C., and then for 3 hours while it is allowed to return to ambient temperature. The reaction mixture is poured onto ice and the precipitate is filtered off and rinsed with water. After drying, the title product is obtained in the form of pale yellow powder.

Melting point: 190–200° C. Elemental microanalysis:

|  | C % | H % | N % | S % | Cl % |
|---|---|---|---|---|---|
| calculated | 37.70 | 3.41 | 3.38 | 7.74 | 17.12 |
| found | 38.04 | 3.47 | 3.40 | 7.74 | 17.16 |

Step F: (7-Chloro-2-oxo-6-sulphamoyl-1,2-dihydro-3-quinolyl)phosphonic Acid Diethyl Ester A suspension of the compound obtained in Step E (1.26 g, 3.0 mmol) in 18 ml of 28 % ammonium hydroxide is stirred. After a few minutes, dissolution is observed. Stirring is continued for 30 minutes and the reaction mixture is acidified with 4N HCl. A few ml of ethyl acetate are added, with stirring, and precipitation is produced. The precipitate is filtered off and dried in vacuole to yield the title product in the form of cream-coloured powder.

Melting point. 288–290° C.

Step G: (7-Chloro-2-oxo-6-sulphamoyl-1, 2-dihydro-3-quinolyl)phosphonic Acid 3.33 ml (25.3 mmol) of bromotrimethylsilane are added to a suspension of the compound obtained in Step F (1.0 g, 2.53 mmol) in 30 ml of anhydrous acetonitrile. The batch is stirred at reflux for 1 hour and evaporated to dryness. The residue is dried in vacuole and is taken up in methanol. The suspension is stirred for 30 minutes, becoming thicker and thicker. After filtering off the white precipitate and rinsing with a little methanol and then ether, the title product is obtained.

Melting point: >300° C.; Elemental microanalysis.

|  | C % | H % | N % | S % |
|---|---|---|---|---|
| calculated | 31.92 | 2.38 | 8.27 | 9.47 |
| found | 31.76 | 2.52 | 7.92 | 9.18 |

EXAMPLE 2

(7-Trifluoromethyl-2-oxo-6-sulphamoyl-1,2-dihydro-3-quinolyl)phosphonic Acid

The procedure is as in Example 1, replacing the 2-amino-4-chloro-benzaldehyde in Step A by 2-amino-4-trifluoromethyl-benzaldehyde, and carrying out the reduction step in Step D with the couple Pd-C/ammonium formate instead of the couple $Fe/NH_4Cl$ in a dilute alcoholic medium.

Step A: [(5-Trifluoromethyl-2-formyl-phenylcarbamoyl)methyl]phosphonic Acid Diethyl Ester Melting point. 62–64° C.; Elemental microanalysis:

|  | C % | H % | N % |
|---|---|---|---|
| calculated | 45.79 | 4.67 | 3.81 |
| found | 45.89 | 4.66 | 3.76 |

Step B: (7-Trifluoromethyl-2-oxo-1, 2-dihydro-3-quinolyl)phosphonic Acid Diethyl Ester Melting point: 151° C.; Elemental microanalysis:

|  | C % | H % | N % |
|---|---|---|---|
| calculated | 48.15 | 4.33 | 4.01 |
| found | 48.19 | 4.32 | 3.92 |

Step C: (7-Trifluoromethyl-6-nitro-2-oxo-1,2-dihydro-3-qiinolyl)phosphonic Acid Diethyl Ester Melting point: 209–215° C.; Elemental microanalysis:

|  | C % | H % | N % |
|---|---|---|---|
| calculated | 42.65 | 3.58 | 7.11 |
| found | 42.86 | 3.58 | 6.78 |

Step D: (6-Amino- 7-trifluoromethyl-2-oxo-1, 2-dihydro-3-quinolyl);phosphonic Acid Diethyl Ester A mixture of 490 mg (1.24 mmol) of the compound obtained in Step C, 650 mg (12.4 mmol) of ammonium formate and 120 mg of 10% Pd/C in 50 ml of ethanol is stirred at reflux for 1 hour. The catalyst is filtered off over a membrane, the filtrate is evaporated to dryness and the residue is taken up in water. The suspension is filtered, rinsed with water, suction-filtered and dried in vacuole to obtain the title product in the form of a yellow solid.

Melting point: 240–244° C.; Elemental microanalysis:

|  | C % | H % | N % |
|---|---|---|---|
| calculated | 46.16 | 4.43 | 7.69 |
| found | 46.26 | 4.37 | 7.62 |

Step E: (7-Trifluoromethyl-6-chlorosulphonyl-2-oxo-1,2-dihydro-3-quinolyl);phosphonic Acid Diethyl Ester Melting point: 165–171° C. Elemental microanalysis:

|  | C % | H % | N % | S % | Cl % |
|---|---|---|---|---|---|
| calculated | 37.56 | 3.15 | 3.13 | 7.16 | 7.92 |
| found | 37.54 | 3.20 | 3.18 | 7.05 | 7.97 |

Step F: (7-Trifluoromethyl-2-oxo-6-sulphamoyl-1,2-dihydro-3-quinolyl);phosphonic Acid Diethyl Ester Melting point: 258–259° C.; Elemental microanalysis:

|  | C % | H % | N % | S % |
|---|---|---|---|---|
| calculated | 39.26 | 3.76 | 6.54 | 7.49 |
| found | 39.54 | 3.65 | 6.46 | 7.35 |

Step G: (7-Trifluoromelhyl-2-oxo-6-sulphamoyl-1, 2-dihydro-3-quinolyl);Phosphonic Acid Melting point:>260° C.; Elemental microanalysis:

|  | C % | H % | N % | S % |
|---|---|---|---|---|
| calculated | 32.27 | 2.17 | 7.53 | 8.61 |
| found | 32.45 | 2.01 | 7.64 | 8.96 |

EXAMPLE 3

(7-Fluoro-2-oxo-6-sulphamoyl-1,2-dihydro-3-quinolyl)phosphonic Acid

The procedure is as in Example 1, replacing the 2-amino-4-chloro-benzaldehyde in Step A by 2-amino-4-fluoro-benzaldehyde.

Step A: [(5-Fluoro-2-formyl-phenylcarbamoyl)methyl]phosphonic Acid Diethyl Ester Non-isolated product (oil) used as such in Step B.

Step B: (7-Fluoro-2-oxo-1,2-dihydro-3-quinolyl)phosphonic Acid Diethyl Ester

Melting point: 230–233° C.

Step C: (7-Fluoro-6-nitro-2-oxo-1,2-dihydro-3-quinolyl) phosphonic Acid Diethyl Ester Melting point: 259–262° C.; Elemental microanalysis:

|            | C %   | H %   | N %   |
|------------|-------|-------|-------|
| calculated | 45.36 | 4.10  | 8.14  |
| found      | 45.40 | 4.28  | 8.06  |

Step D: (6-A mino-7-fluoro-2-oxo-1,2-dihydro-3-quinolyl) phosphonic Acid Diethyl Ester Melting point: 253–257° C.; Elemental microanalysis:

|            | C %   | H %   | N %   |
|------------|-------|-------|-------|
| calculated | 49.69 | 5.13  | 8.91  |
| found      | 49.52 | 5.28  | 8.70  |

Step E: (7-Fluoro-6-chlorosulphonyl-2-oxo-1,2-dihydro-3-quinolyl)phosphonic Acid Diethyl Ester Melting point: 159–160° C.; Elemental microanalysis.

|            | C %   | H %   | N %   | S %   | Cl %  |
|------------|-------|-------|-------|-------|-------|
| calculated | 39.26 | 3.55  | 3.52  | 8.06  | 8.91  |
| found      | 39.74 | 3.73  | 3.74  | 7.85  | 8.59  |

Step F: (7-Fluoro-2-oxo-6-sulphamoyl-1,2-dihydro-3-quinolyl)phosphonic Acid Diethyl Ester Melting point: 266–268° C.; Elemental microanalysis:

|            | C %   | H %   | N %   | S %   |
|------------|-------|-------|-------|-------|
| calculated | 41.27 | 4.26  | 7.40  | 8.48  |
| found      | 41.17 | 4.48  | 7.17  | 8.34  |

Step G: (7-Fluoro-2-oxo-6-sulphamoyl-1,2-dihydro-3-quinolyl)phosphonic Acid

Melting point: >300° C.; Elemental microanalysis:

|            | C %   | H %   | N %   | S %   |
|------------|-------|-------|-------|-------|
| calculated | 33.55 | 2.50  | 8.69  | 9.95  |
| found      | 33.51 | 2.73  | 8.48  | 9.56  |

PHARMACOLOGICAL STUDY

EXAMPLE A

Inhibition of the Current Induced by Administration of (R,S)-AMPA (10 μM) to Xenopus Oocytes Injected with mRNAs of Rat Cortex Xenopus oocytes are injected with 50 ng of poly (A+) mRNAs isolated from the cerebral cortex of rat and incubated for 2 to 3 days at 118° C. to enable their protein expression. The influx currents induced by an administration of (R,S)-AMPA (10 μM) are measured in a medium having the composition: NaCl (82.5 mM), KCl (2.5 mM), $CaCl_2$ (1 mM), $MgCl_2$ (1 mM), $NaH_2PO_4$ (1 mM), HEPES (5 mM), pH 7.4, by the 2-electrode voltage clamp method (potential=−60 mV). The products of the present invention are administered in a concentration-dependent manner 30 seconds before and during administration of the agonist (R,S)-AMPA.

Their capacity to inhibit the current induced by (R,S)-AMPA is determined by the $IC_{50}$ values (μM), which represent the concentrations that inhibit by 50% the current induced by an administration of (R,S)-AMPA (10 μM).

The compounds of the invention demonstrate excellent inhibitory properties with $IC_{50}$ values (μM) of the order of 0.1.

EXAMPLE B

Audiogenic Convulsion Test in the DBA/2 Mouse

In the immature DBA/2 mouse, convulsive attacks can be triggered by subjecting the animal to stimulation with high-intensity high-frequency sound.

The AMPA-type glutamate receptor antagonists antagonise that type of convulsion in a dose-dependent manner (Chapman et al., Epilepsy Res., 1991, 9, 92–96). This test is used to study the anti-convulsive effects of the compounds of the present invention. In brief, immature DBA/2 mice (21–28 days) are exposed for 60 seconds to a noise of 105 dB and 18 kHz. This causes the appearance of clonic convulsions. The products being studied and the solvent are administered by the i.p. route 30 minutes before the start of the test in a volume of 0.1 ml/10 g. The $ED_{50}$ value (dose that inhibits the occurrence of the convulsions by 50%) is determined for each compound using the method of Litchfield and Wicoxon (J. Pharmacol. Exp. Ther., 1949, 96, 99–113).

The compounds of the invention demonstrate an excellent capacity to inhibit the convulsions with $ED_{50}$ values of the order of 3 mg/kg i.p.

EXAMPLE C

Nephrotoxicity Test in the Fischer Rat

Assessment of the renal impact of the compounds of the present invention is carried out in adult male Fischer rats weighing 200–250 g. Fischer rats are anaesthetised using pentobarbital (Nembutal®, 60 mg/kg i.p.). 90 minutes after anaesthesia has been induced, the test compounds are administered by the intravenous route in doses of 3, 10 and 15 mg/kg. Twenty-four hours after administration, the animals are sacrificed, the plasma is removed and measurements of creatinaemia and uraemia are performed. Statistical analysis is carried out using single-factor variance analysis followed by a Newman-Keuls test, comparing the treated animals and animals having received only the carrier.

The compounds of the invention exhibit excellent renal tolerance, no toxic effect being obtained for doses less than or equal to 15 mg/kg i.v.

EXAMPLE D

Pharmaceutical Composition 1000 tablets containing a dose of 5 mg of(7-chloro-2-oxo-6-sulphamoyl-1,2-dihydro-3-quinolyl) phosphonic acid (Example 1) . . . 5 g Wheat starch . . . 20 g
Maize starch . . . 20 g
Lactose . . . 30 g
Magnesium stearate . . . 2 g
Silica . . . 1 g
Hydroxypropylcellulose . . . 2 g

We claim:

1. A compound selected from those of formula (I):

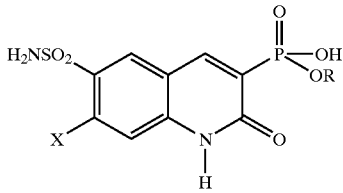

wherein:

X represents chlorine or fluorine or trifluoromethyl,

R represents hydrogen or a group

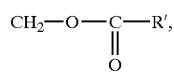

wherein R' represents hydrogen or linear or branched ($C_1$–$C_6$) alkyl or phenyl, its isomers and addition salt thereof with a pharmaceutically acceptable base.

2. A compound selected from those of claim 1 wherein R represents hydrogen.

3. A compound selected from those of claim 1 which is (7-chloro-2-oxo-6-sulphamoyl-1,2-dihydro-3-quinolyl) phosphonic acid, its isomers and addition salt thereof with a pharmaceutically acceptable base.

4. A compound selected from those of claim 1 which is (7-trifluoromethyl-2-oxo-6-sulphamoyl-1,2-dihydro-3-quinolyl) phosphonic acid, its isomers and addition salt thereof with a pharmaceutically acceptable base.

5. A compound selected from those of claim 1 which is (7-fluoro-2-oxo-6-sulphamoyl-1,2-dihydro-3-quinolyl) phosphonic acid, its isomers and addition salt thereof with a pharmaceutically acceptable base.

6. A method for treating an animal or human living body afflicted with stroke, cerebral or spinal trauma, and epilepsy comprising the step of administering to the living body an amount of a compound of claim 1 which is effective for alleviation of said condition.

7. A pharmaceutical composition comprising as active principle an effective amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,518,258 B1
DATED : February 11, 2003
INVENTOR(S) : Alex Cordi, Patrice Desos and Pierre Lestage It is certified that error appears in the above-identified patent and that said Letters Patent is hereby corrected as shown below:

<u>Title page,</u>
Item [54], Title, "QUINOLYPHOSPHONIC" should read
-- QUINOLYLPHOSPHONIC --

Signed and Sealed this

Third Day of June, 2003

JAMES E. ROGAN
*Director of the United States Patent and Trademark Office*